United States Patent [19]
Morris

[11] Patent Number: 5,251,627
[45] Date of Patent: Oct. 12, 1993

[54] NON-INVASIVE MEASUREMENT OF EYEBALL PRESSURE USING VIBRATION

[76] Inventor: Donald E. Morris, 44 Marguerita Rd., Kensington, Calif. 94707

[21] Appl. No.: 722,036

[22] Filed: Jun. 27, 1991

[51] Int. Cl.$^5$ .............................................. A61B 3/16
[52] U.S. Cl. ................................. 128/645; 128/649
[58] Field of Search ................................. 128/645–649

[56] References Cited

U.S. PATENT DOCUMENTS

| | | | |
|---|---|---|---|
| 3,613,666 | 10/1971 | Hobbs | 128/2 |
| 3,690,158 | 9/1972 | Lichtenstein et al. | 73/80 |
| 3,763,696 | 10/1973 | Krakau | 73/80 |
| 4,576,176 | 3/1986 | Myers | 128/660 |

FOREIGN PATENT DOCUMENTS

933073  6/1982 U.S.S.R.
982649 12/1982 U.S.S.R.

OTHER PUBLICATIONS

Krakau, *Exp. Eye Res.*, (1971) 11:140 (Abstract).
Roth et al., *J. Am. Opometric Assoc.* (1963) 34:971–974.
Guttmann et al., *J. Am. Optometric Assoc.* (1963) 34:975–977.

*Primary Examiner*—Randy C. Shay
*Attorney, Agent, or Firm*—Townsend and Townsend Khourie and Crew

[57] ABSTRACT

A tonometer. The tonometer includes means (6) for generating a surface wave on the eye. The surface wave is monitored at a receiving transducer (10) and phase information is extracted using a phase meter (14). Using the phase information the velocity of the wave may be determined and from this information the pressure in the eyeball may be determined in signal processor (16). The eyeball pressure may be displayed in display (18).

7 Claims, 4 Drawing Sheets

NON-INVASIVE MEASUREMENT OF EYEBALL PRESSURE USING VIBRATION

BACKGROUND OF THE INVENTION

The present invention relates to the field of methods and devices for evaluation of the eyeball. More specifically, in one embodiment the invention provides an improved method and device for measurement of pressure in the eyeball, otherwise known as a tonometer which is especially safe and easy to use, enabling home use in some embodiments.

Measurement of the pressure in the eyeball is necessary in connection with the diagnosis, evaluation, and control of glaucoma. Glaucoma is the group of ocular diseases having in common an elevation or instability (diurnal variation) in intraocular pressure beyond the tolerance of the eyeball. In many patients, glaucoma is controlled by medication, and regular monitoring of intraocular pressure can be beneficial in management of these patients.

Instruments for measurement of the intraocular pressure are known as tonometers. There are two commonly used types, those which contact the eyeball and those which do not. Both types are used by a professional and require an office visit by the patient. In the aplanation contact tonometer, a flat-ended probe is placed in contact with the cornea or sclera. Then the probe is pressed against the eyeball to produce a flattened area of specified diameter. The applied force is measured, and the pressure is calculated. In the non-contact tonometer a puff of air is directed onto the surface of the eyeball, and the deflection of the surface is measured optically. Both of these methods are applicable to a clinical setting and require a trained professional to take the measurement. Frequent self monitoring of intraocular pressure by glaucoma patients could be useful for early detection of a sudden pressure rise.

A vibration tonometer has been proposed. According to one such device, the resonant frequency of a vibrating mass placed in contact with the eyeball is used. The eyeball surface provides the spring-restoring force for the vibration, and thus determines the resonant frequency of the system. The intraocular pressure determines the stiffness of the "spring." Unfortunately, since the eyelid is very soft and compressible, the measurement must be made with the probe end in direct contact with the eyeball so that the eyelid compressibility will not substantially impact the measurement. As a result this "vibration tonometer" is generally a contact type instrument, and would typically be used in a professional setting.

Another type of vibration tonometer (which also requires contact with the cornea) utilizes a forced vibration of 20 Hz frequency and 0.01 mm amplitude which is applied to the cornea, and the counter pressure is measured by a piezoelectric crystal. According to a variation of this method, the probe, which touches the eyeball, is driven by a dynamic (moving coil) system such as used in loud-speakers, and a piezoelectric pressure transducer measures the reaction pressure of the eyeball. According to other variations, the vibrating mass is replaced with a piezoelectric quartz disc coupled to a quartz membrane placed in contact with the cornea. Such systems suffer from a number of restrictions. For example, accuracy of the device would be significantly impacted if the device is not used in direct contact with the eyeball.

A vibration-based tonometer has also been described in which a vibrator is placed on the eyelid near its edge, and is driven at ultrasonic frequencies around 25–30 kHz. The waves produced by such a device are on the order of the resonance frequency for compressive body waves in the eyeball, since compressive waves travel at about $3 \times 10^5$ cm/s in water, and the distance from the front to the rear of the eyeball is 2.4 to 3 cm. The vibration is detected by a light beam which is directed on the cornea and reflects onto a photo detector, and the intraocular pressure is intended to be determined from the amplitude of the vibrations induced in the eyeball. Again, amplitude of the waves will be impacted by the eyelid, thereby impacting the accuracy of the device.

It has also been proposed to measure intraocular pressure by the speed with which mechanical oscillations spread across the surface of the eyeball. The eyelid is kept closed, and transmitting and receiving transducers are placed some distance apart on the eyelid above the cornea. The intraocular pressure is determined by the elapsed time of arrival of surface waves started at a specific time. The transmitter is triggered and a wave train is switched on. On reaching the receiver the wave is displayed on an oscilloscope triggered along with the transmitter. Unfortunately, a wave train which is suddenly switched on will generally contain a range of frequencies. Furthermore, surface wave propagation is dispersive (the velocity depends on frequency). As a consequence, the constituent waves will arrive with different delays, and when they are recombined to form the received wave train, it will not have a sharp onset. As a result the intraocular pressure will not be accurately determined.

For example, if a frequency of 5 kHz is employed, the wavelength of the waves is about $\lambda \approx 4$ cm. Therefore, from $v = \nu \lambda$ (velocity = frequency·wavelength) and $T = S/v$ (time = distance/velocity), the calculated transit time $T \approx 10$ msec for the largest feasible transmitter-receiver separation $S \approx 2$ cm, and there will be $\sim 50$ waves on the cornea between the transmitter and receiver. Solving for eyeball pressure using this information and differentiating, it is found that $\Delta p/p = -3 \Delta T/T$ (from equation 2, below). Therefore if the intraocular pressure is to be measured to 10% accuracy, the arrival time would need to be measured to within 3.2%, i.e., 320 $\mu$sec. For this to be possible, the rise time of the signal at the receiver should be less than 320 $\mu$sec. This in turn requires the amplitude modulation of the 5 kHz signal to include sidebands up to $\sim \pm 1500$ Hz, as can be shown by Fourier analysis. So long as $\lambda < 5$ cm, $v = \lambda \nu = (\pi r p/\lambda)^{\frac{1}{2}}$ (where v is wave velocity of propagation, r is eyeball radius, p is eyeball pressure, and $\nu$ is wave frequency) so velocities would be spread out about $(5000 \pm 1500 \text{ Hz})^{\frac{1}{2}}/(5000 \text{ Hz})^{\frac{1}{2}} = (1 \pm 0.3)^{\frac{1}{2}}$, i.e., about $\pm 9\%$. As a result, the transit times of the various Fourier components will also be spread out by the same factor or a total of about 1800 $\mu$sec. This is far larger than the allowable range of 320 $\mu$sec. In fact, with the parameters given above, the accuracy of pressure measurement by this method would be expected to be relatively low, such as below about 30%, as may be seen by substitution in the above calculations.

To achieve a 10% accuracy, the frequency would have to be increased above 25 kHz. However, this is on the order of the resonance frequency for compressive body waves which travel from the front to the rear of the eyeball. The compression waves reflected from the rear of the eyeball would reach the receiver very quickly, and thus, resonant compression vibrations of the eyeball would give spurious readings. It is clear that measurement of elapsed time until arrival of surface waves started at a specific time is not an appropriate method for accurate determination of intraocular pressure.

From the above it is seen that an improved tonometer and method of measuring pressure of the eyeball is needed.

SUMMARY OF THE INVENTION

An improved tonometer and method of determining eye pressure is provided by virtue of the present invention. According to preferred aspects of the invention, the device is non-invasive (i.e., does not require direct contact with the eyeball). Therefore, the device may be used conveniently with little or no professional assistance. The non-invasive tonometer operates on the physical principle that surface tension of a material determines the velocity of propagation of a surface wave on a fluid.

The invention provides for generation of an appropriate continuous wave at or near the surface of the eyeball using a transducer. By "continuous wave" it is intended to mean herein that the wave-generating transducer generates a wave of constant selected frequency over a time period sufficient to create a steady state traveling or standing wave along the surface of the eyeball. The wave is monitored at one or more locations displaced from the transducer for phase change information using, for example, a phase-sensitive detector. Using the phase change information, the velocity of the wave across the surface of the eyeball may be determined. This information may further be used to determine the pressure in the eyeball.

Accordingly, in one embodiment the invention provides apparatus for determining the internal pressure in an eyeball comprising means for applying continuously varying mechanical waves at a first location on an eyeball; means for detecting the waves at a second location on the eyeball, the means for detecting adapted to determine a phase of the waves at the second location; and signal processing means coupled to the means for detecting including means for determining a velocity of the waves on the eyeball between the first and second locations on the eyeball based on the phase of the waves and adapted to use the velocity of the waves and output a value representative of pressure in the eyeball.

A further understanding of the nature and advantages of the inventions herein may be realized by reference to the remaining portions of the specification and the attached drawings.

DESCRIPTION OF THE PREFERRED EMBODIMENTS

Figure 1:
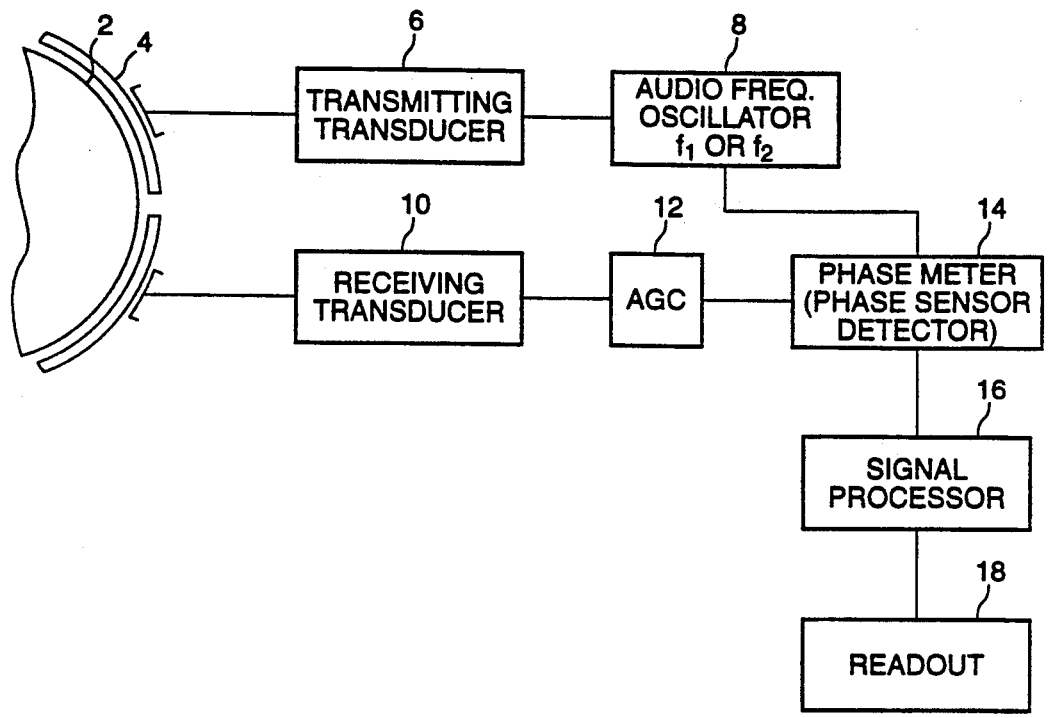
FIG. 1 is a schematic illustration of the invention using a single transmitter and a single receiver.

The present invention provides a new method and apparatus type of surface wave tonometer, which generally operates using the phase delay in propagation of a continuous sine wave over the surface of the cornea or sclera. The non-invasive tonometer operates on the physical principle that surface tension of a material determines the velocity of propagation of a surface wave on a fluid. A transmitting transducer is placed on the eyelid and generates a desired vibrational frequency in the surface of the eyeball. A receiving transducer is placed at a location displaced from the transmitting transducer, and measures phase delay information in the wave. The meter may be used without direct contact to the eyeball, without substantially affecting the accuracy of its measurement since the compressibility of the eyelid will tend to reduce only the amplitude of the surface wave produced on the eyeball and not substantially impact the phase information used herein.

According to one preferred embodiment of the invention, the effects of compliance of the eyelid are reduced even further by performing the measurement with two receiving transducers placed at different fixed distances from the transmitter, and the phase difference between their outputs is used to determine the surface wave velocity. The receiver phase is not affected by the eyelid when the compliance of the receiving transducer is sufficiently high.

Since the transmitting transducer placed on the eyelid may press on the eyeball excessively if not used carefully (thereby affecting pressure in the eyeball), according to one embodiment this problem is avoided by using a non-contact transmitting transducer. For example, a periodically pulsating air jet from a nozzle placed close to the front of the eyeball is used in some embodiments to set up periodic surface waves which spread over the surface of the cornea and the eyeball. Of course, any transducer which produces localized compression waves in the air (such as a loudspeaker with a loading horn or nozzle) can be used instead of the pulsating air jet without deviating from the scope of the invention. The distance from the eyeball and the intensity of the pulsations is not critical, since unlike the non-contact tonometers used previously in which a puff of air is directed onto the surface of the eyeball, the magnitude of the deflection of the surface of the eyeball need not be measured, but only the phase velocity of the induced surface waves across the surface of the eyeball.

In some embodiments, the invention also employs a non-contacting type of receiving transducer. The coupling to the transducer need not be held constant or calibrated since only the phase and not the amplitude of surface vibration is required to be measured according to this invention. Therefore, it is not necessary to position the transducer at an accurately known or controlled distance from the eyeball. Several possible types of transducers can be utilized. For example, an infrared or visible light beam can be directed onto the cornea or sclera and the deflection of the reflected beam caused by the surface wave passing the illuminated area can be monitored by photo-detectors. Another embodiment of the invention measures the capacitance between a probe placed close to the surface of the eyeball. This is accomplished by a high-frequency capacitance meter, since tissue is a fairly good conductor. Therefore, the electromagnetic "skin depth" in tissue is very small at high frequencies. The capacitance will vary periodically as the surface waves pass across the eyeball surface under the probe.

Another embodiment of the invention employs a high-frequency inductor or mutual inductance close to the eyeball surface in detection of the received wave. The self inductance of the coil or the mutual inductance between two coils vary as the surface wave passes.

In another embodiment of the invention, a high-frequency ultrasound wave is directed onto the eyeball and reflected from the surface in detection of the received wave. The echo return time or phase will vary as the eyeball surface vibrated. Any timing error due to the transit time of the ultrasound from the generator to the eyeball and back would be negligible, since the velocity of sound waves in air (about $3 \times 10^4$ cm/s) is far greater than the velocity of surface waves on the eyeball. To avoid errors due to phase shift at the transmitter, two non-contacting receiving transducers can be spaced apart to determine the surface wave velocity.

FIG. 1 illustrates one embodiment of the invention. In FIG. 1 the eyeball 2 is covered by the eyelid 4. A vibrating transducer 6 driven by an audio frequency oscillator 8 is placed on the lid and pressed lightly thereon to produce surface waves across the eyeball. A second transducer 10 is also pressed lightly against the eyelid at a small distance (e.g., 0.2-2 cm) from the first transducer to detect the surface vibrations. The distance between the transmitter and receiver, or between two receivers, is known and used in calculation of eye pressure according to some embodiments.

The velocity of the surface wave is determined by measurement of the phase shift of the surface wave between the driving transducer and the receiving transducer. In particular, the received wave is processed through an automatic gain controlled (AGC) amplifier 12 and thereafter its phase is compared to the original wave at a phase meter 14. To separate the effect of the mass and stiffness of the cornea and/or sclera, the measurement is made at several frequencies in preferred embodiments. Measurement at several frequencies eliminates the effect of the cornea and/or sclera because the highest frequency measurements will be most affected by the sclera. The phase shift information is processed through a signal processor 16 such as discrete logic or an appropriately programmed digital microprocessor (or a combination thereof) to determine pressure in the eye in accordance with the techniques disclosed herein. This information is output to a readout 18 such as a cathode ray tube, LCD display, LED display, or the like.

In operation, source 8 generates a continuously varying sine wave signal of a selected frequency and outputs this signal to oscillator 6. Oscillator 6 vibrates continuously at the selected frequency, thereby generating surface waves in the eyeball 2 through the eyelid 4. These surface waves are transmitted across the surface of the eyeball, transmitted back through the eyelid, and received by the receiving transducer 10. The signals from the receiving transducer are amplified and limited in AGC amplifier 12 and output to the phase meter ("phase-sensitive" detector or "lock-in" detector) 14. The phase meter 14 (such as a phase meter available from Stanford Research) outputs a digital or analog signal representative of the difference between the phase of the wave at the location of the second transducer compared to the phase at the transmitter (reference signal). The velocity of the wave is then resolved.

Accordingly (given that variations in pressure in the eyeball will not be of sufficient magnitude to shift a wave more than a full cycle) the phase shift from this baseline value may be used to determine the wavelength and, therefore, the velocity of the wave (since the applied frequency is known). In some embodiments, sufficiently low frequencies are used such that there is less than one cycle between the transmitter and receiver. This eliminates any problems related to wave "counting." Based upon the velocity of the wave, its frequency, and the size of the persons eye, it becomes possible to Calculate in the signal processor 16 the pressure in the eyeball according to the technique below.

Figure 2:
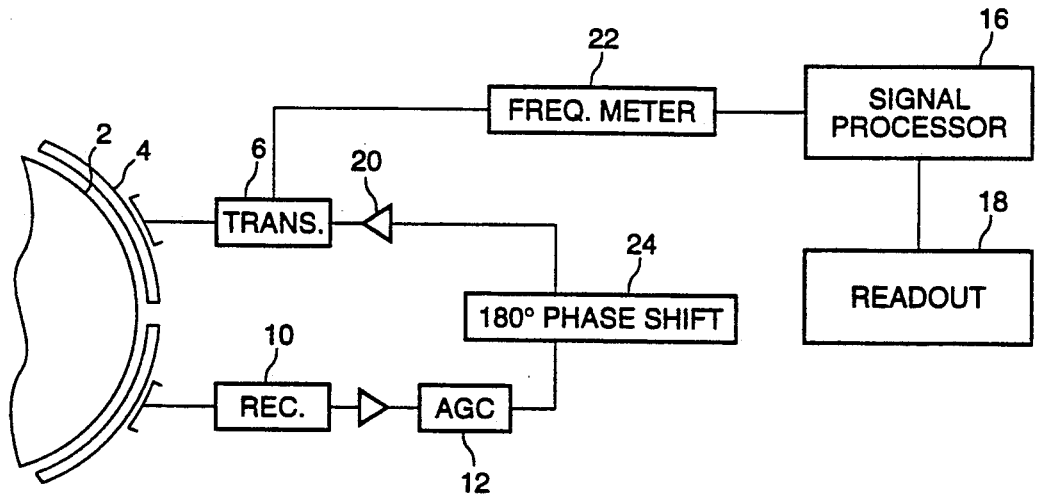
FIG. 2 is a schematic illustration of the invention utilizing frequency sweep to determine the frequency at which a specified phase shift is obtained.

In an alternative embodiment of this invention, the frequency is automatically varied or swept until a predetermined phase is found. The alternative embodiment of the invention is shown in FIG. 2. According to this embodiment, the transmitting transducer is driven by an amplifier 20 with feedback provided by the receiving transducer. An amplifier may also be provided for the receiving transducer output. A frequency meter 22 determines the frequency at which the phase is shifted an appropriate amount. The frequency of oscillation will be determined by the (frequency-dependent) phase delay in the surface wave between the two transducers. In case the transducers are connected to the input and output of the amplifier in opposite phase, the circuit will oscillate at a frequency at which the phase delay in the surface wave is 180°. The intraocular pressure is then given by the oscillation frequency according to the methods herein.

The velocity of surface waves in a fluid is known. This is applied herein for surface tension dominated waves. For surface tension dominated surface waves I have derived:

$$v = \nu\lambda = (2\pi\tau/\lambda\rho)^{\frac{1}{2}} (\tanh 2\pi h/\lambda)^{\frac{1}{2}} \qquad (1)$$

where $\tau$ is surface tension, v is the velocity of propagation of the wave of frequency $\nu$ and wavelength $\lambda$, $\rho$ is density of the eye, and h is the depth of the liquid in the medium in which it is travelling. On a sphere, the surface tension $\tau = pr/2$, where p is the pressure and r is the radius of the sphere (eyeball) which varies from person to person. Measurement of the surface tension $\tau = pr/2$ by determination of the surface wave velocity therefore gives the pressure if the radius of curvature of the eyeball is known. The above Equation (1) is derived for waves on a flat surface, and so it is most accurate for wavelengths substantially shorter than the radius of the eyeball. The depth h is taken as approximately equal to the radius of the eyeball ($r \approx 1.5$ cm). For $\lambda < 5$ cm, the second term $(\tanh 2\pi h/\lambda)^{\frac{1}{2}}$ is between 0.98 and 1.00. The density $\rho$ of the eyeball is nearly 1.00 g/cm$^3$. Then Equation (1) simplifies to $v = \nu\lambda = (\pi pr/\lambda)^{\frac{1}{2}}$, from which $\lambda = (\pi rp)^{\frac{1}{3}}/\nu^{\frac{2}{3}}$ and the pressure in the eyeball simplifies to an equation of the form:

$$p = \lambda^3 \nu^2/\pi r \qquad (2)$$

z / xr (2)

The phase difference will be the fraction of a wavelength between the two positions. Since the distance between the two positions is known, wavelength will be known. Having determined the wavelength, and knowing the frequency, the velocity of the wave can be determined. Preferably, the wave is chosen to have a sufficiently long wavelength to unambiguously determine the wavelength between the two positions.

It should be noted that the surface wave propagation is dispersive, i.e., the velocity depends on the frequency. Therefore, the measurement is made at discrete frequencies in preferred embodiments using periodic waves. It will be readily apparent that variations in the exact form of the above equation via the addition of constants and the like will be encompassed within the scope of the present invention.

Waves applied to the eyeball using the invention herein are preferably applied in a continuous manner. Waves applied as a pulse would generally be undesirable because a pulse would "spread out," since the Fourier components of different frequencies travel at different velocities. Therefore an accurate measurement of the arrival time would be extremely difficult. Further, the measured surface wave velocity would depend on the frequency content of the initial pulse, attenuation of the various frequencies during propagation, the frequency dependence of sensitivity of the receiving transducer, and the bandwidth of the electronics. The resulting measurement would be uncertain and ambiguous. According to some embodiments, a pulse having the shape of $(sine(x)/x)^2$ is used to limit bandwidth of a pulsed input. A shaped pulse in this manner is used instead of a continuous wave. According to this embodiment, the arrival time of the lowest frequency is soonest, since velocity decreases with higher frequency and arrival time can be used to determine pressure in the eyeball. By using a predetermined shape of pulse, it becomes possible to unambiguously detect the arrival time of a selected component of the pulse.

The normal intraocular pressure in the non-glaucoma population is 15.4 ±2.5 torr (sitting) and 16±2.6 torr (reclining) (A. E. Kolker, U J. Hetherington, "Diagnosis and Therapy of the Glaucomas," 1976, page 59, which is incorporated herein by reference). Intraocular pressure greater than 21 torr (by aplanation method) is found in 4.7 to 6.5% of normal eyes, and in 80% of eyes with untreated glaucoma. Taking 16 torr as normal and 21 torr as indicative of borderline glaucoma, the following tabulated values are calculated for eyeballs with radii of 1.2 cm and 1.5 cm, and at intraocular pressures of 16 torr (normal) and 21 torr (borderline glaucoma).

individual's eye. Thereafter, the measurements of the system are adjusted by the same factor.

Figure 3:
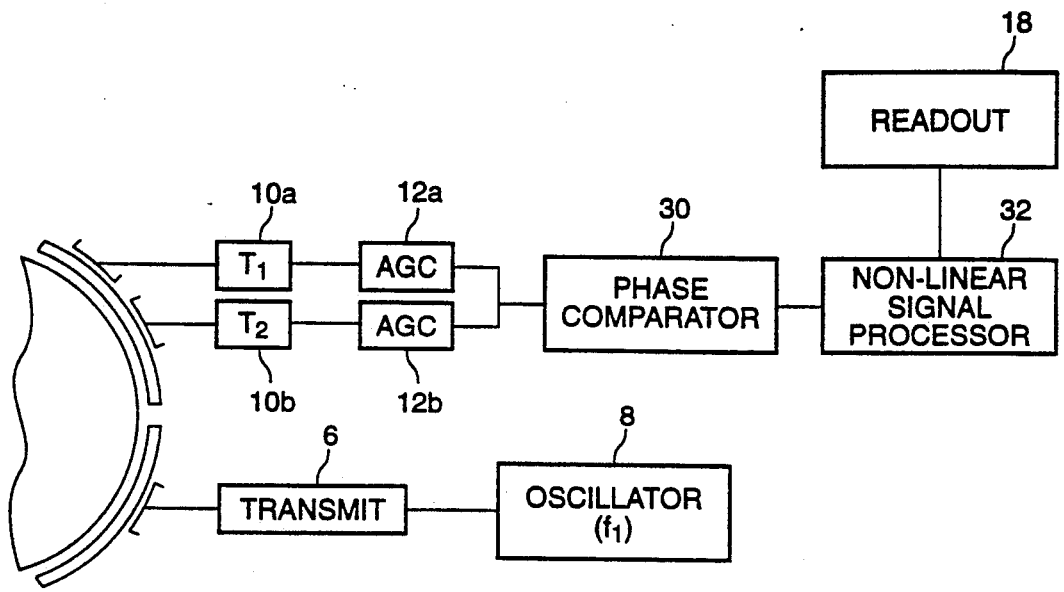
FIG. 3 is a schematic illustration of the invention using two receiving transducers.

FIG. 3 illustrates another alternative embodiment of the invention herein. This embodiment will tend to eliminate the small effect of phase shift in the eyelid. According to this embodiment, the transmitting transducer 6 is placed at a distance from first receiving transducer 10a and second receiving transducer 10b. The receiving transducers are separated from the transmitter and each other by known distances. After passing through AGC's 12a and 12b, the signals from the receiving transducers are compared in phase comparator 30. Signals from the phase comparator 30 are processed in non-linear signal processor 32 in which the difference in phase at the two receiving transducers is used to calculate the surface wave velocity. The receiver phase is not affected by the eyelid so long as the compliance of the receiving transducer is sufficiently high. This is assured through the use of a highly compliant transducer such as a moving coil or moving magnetic microphone.

Figure 4:
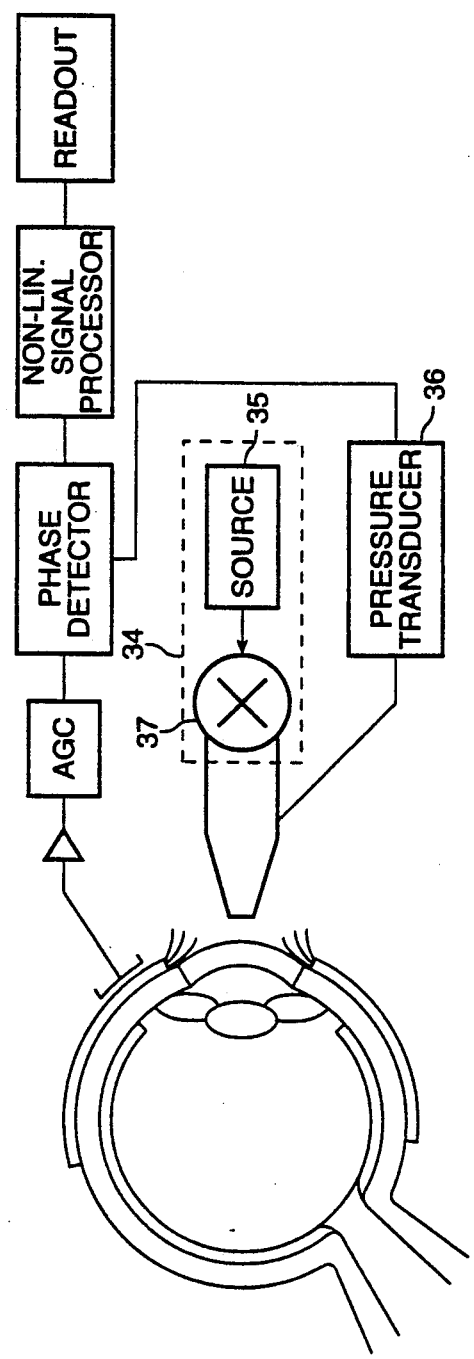
FIG. 4 illustrates an alternative embodiment using an air source.

FIG. 4 illustrates another embodiment of the invention. According to this embodiment the transmitting transducer is replaced with a pulsating air source 34, the output of which is monitored by pressure transducer 36. The pulsating air source 34 includes a constant air source 35 and pressure controlling valve 37. As with the first embodiment, the velocity of the surface waves induced in the eyeball are used to determine the pressure in the eyeball.

Figure 5:
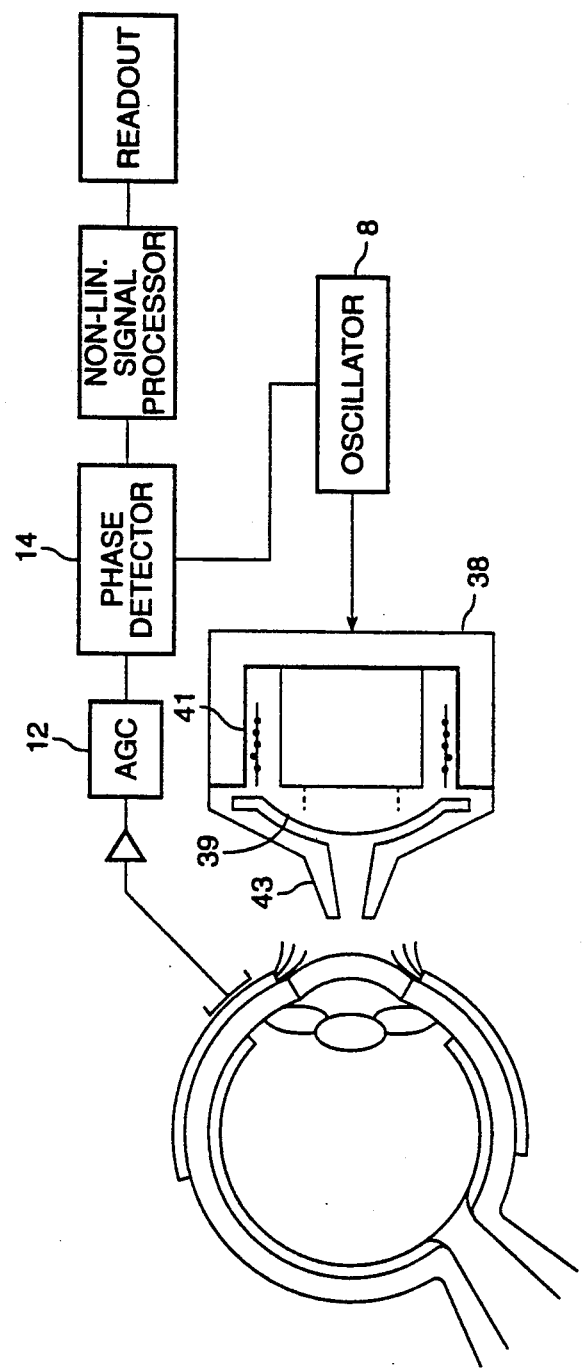
FIG. 5 illustrates an alternative embodiment of the invention using a non-contacting transmitter.

FIG. 5 illustrates another embodiment of the invention. According to this embodiment of the invention, the transmitting transducer is replaced with a non-contacting transducer 38 such as an audio transmitter. Coupling of the audio frequency vibrations need not be efficient since only the phase information in the received wave will be utilized; not the amplitude information. The transducer 38 includes a vibrating diaphragm 39 and driver 41. Oscillations are concentrated on the eye via horn-shaped assembly 43.

Figure 6:
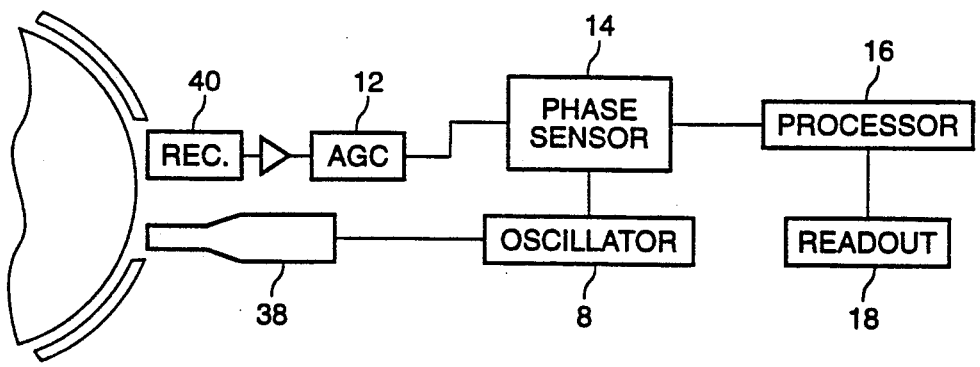
FIG. 6 illustrates an alternative embodiment of the invention using both a non-contacting transmitter and receiver.

It will also be possible to utilize non-contacting receiving transducers in accordance with some embodiments of the invention, as shown in FIG. 6. According to these embodiments, the receiving transducer 40 is, for example, composed of an infrared light source that is directed at the cornea or sclera of the eye and the deflection of the reflected beam caused by the surface wave passing underneath the illuminated area is monitored by photodetectors. In still further alternative embodiments, the receiving transducer 40 is composed of a high frequency (e.g., greater than 40 kHz) capacitance meter placed on the eye or eyelid. According to these embodiments, the skin depth of the tissue will be small in view of the high frequency of the meter operation and the capacitance will vary periodically as the surface waves pass across the eyeball surface under the probe.

TABLE I

| Frequency | Intraocular Pressure p = 16 torr | | | | Intraocular Pressure p = 21 torr | | | |
|---|---|---|---|---|---|---|---|---|
| | r = 1.2 cm | | r = 1.5 cm | | r = 1.2 cm | | r = 1.5 cm | |
| ν | λ | v | λ | v | λ | v | λ | v |
| 20.5 Hz | 1.62 cm | 33.2 cm/s | 1.83 | 37.5 | 1.86 | 38.1 | 2 | 41 |
| 58 | 0.81 | 47 | 0.91 | 53 | 0.93 | 54 | 1 | 58 |
| 164 | 0.41 | 66 | 0.46 | 75 | 0.47 | 76 | 0.5 | 82 |
| 647 | 0.16 | 105 | 0.18 | 118 | 0.19 | 120 | 0.2 | 130 |
| 1830 | 0.08 | 148 | 0.09 | 167 | 0.09 | 170 | 0.1 | 183 |
| 5175 | 0.04 | 210 | 0.046 | 237 | 0.046 | 241 | 0.05 | 259 |

It is seen from Table I that v and λ are both larger when the intraocular pressure p=21 torr (borderline Glaucoma). The above calculations neglect the thickness, mass and stiffness of the sclera, variations in the thickness of the sclera, and the deviation of the eyeball from a sphere. In some embodiments, the device is calibrated for the individual eye at the time the intraocular pressure is measured by a professional using a conventional tonometer to derive an adjustment factor for an According to still further embodiments, the receiver employs a high frequency inductor or mutual inductance close to the eyeball surface in which the inductance of two coils will vary as the surface wave passes. In still further embodiments, high frequency ultrasound waves are directed onto the eyelid which are reflected from the surface. The echo return time or phase will vary as the eyeball surface vibrates. Any timing error due to the transit time of the ultrasound from the generator to the eyeball is negligible since the velocity of the sound waves in air is far greater than the velocity of the surface waves on the eyeball.

Conclusion

The invention provides a non-invasive surface wave tonometer which may be used by a doctor or patient to monitor pressure in the eye. The above description is illustrative and not restrictive. Many variations of the invention will become apparent to those of skill in the art upon review of this disclosure. Merely by way of example, specific manufacturers of various devices used herein have been disclosed for the purpose of illustrating the invention, but a wide variety of devices will be used in various implementations. By way of further example the equations shown herein are exemplary of those which may be used in performing the calculations necessary for glaucoma testing. Other equations may be utilized, or additional factors, constants, and the like may be necessary in particular circumstances. The scope of the invention should, therefore, be determined not with reference to the above description, but instead should be determined with reference to the appended claims along with their full scope of equivalents.

What is claimed is:

1. A method for determining the internal pressure in an eyeball comprising:
    a) applying continuously varying mechanical waves at a first location on an eyeball;
    b) detecting said waves at a second location on said eyeball, said detecting step determining a phase of said waves at said second location;
    c) determining a velocity of said waves on said eyeball between said first and second locations on said eyeball based on said phase of said waves;
    d) using said velocity of said waves to determine pressure in said eyeball; and
    e) displaying said eyeball pressure.

2. The method as recited in claim 1 wherein said step of applying continuously varying mechanical waves is a step of applying waves to the eyelid.

3. The method as recited in claim 1 wherein said step of applying is a step of applying waves with a frequency of between about 20 Hz and 5000 Hz.

4. A method for determining internal pressure in an eyeball comprising:
    a) applying at a first location on said eyeball a pulse having a shape defined by an equation of a predetermined form;
    b) detecting waves at a second location on said eyeball; and
    c) processing information regarding a wave form of waves so detected in conjunction with information regarding said shape defined by said equation of said predetermined form, said equation of said predetermined form being chosen to make possible the detection of the arrival time at said second location of a selected frequency component of said wave form of waves so detected, so as to determine a velocity of waves on said eyeball, and to determine a pressure in said eyeball.

5. The method of claim 4 in which said equation of said predetermined form is chosen so as to limit the bandwidth of said pulse.

6. The method of claim 4 in which said predetermined form is the form $(\sine(x)/x)^2$.

7. The method of claim 4 in which said pulse is applied to said eyeball through an eyelid overlying said eyeball.

* * * * *